United States Patent
Schwartz

(10) Patent No.: US 10,933,544 B2
(45) Date of Patent: Mar. 2, 2021

(54) GUILLOTINE STYLE CUTTING MECHANISM

(71) Applicant: Todd Schwartz, Meadowbrook, PA (US)

(72) Inventor: Todd Schwartz, Meadowbrook, PA (US)

(*) Notice: Subject to any disclaimer, the term of this patent is extended or adjusted under 35 U.S.C. 154(b) by 0 days.

(21) Appl. No.: 15/383,816

(22) Filed: Dec. 19, 2016

(65) Prior Publication Data

US 2017/0232623 A1 Aug. 17, 2017

Related U.S. Application Data

(60) Provisional application No. 62/268,576, filed on Dec. 17, 2015.

(51) Int. Cl.
*B26B 17/00* (2006.01)
*A61B 17/32* (2006.01)
(Continued)

(52) U.S. Cl.
CPC .......... *B26B 17/00* (2013.01); *A61B 17/0467* (2013.01); *A61B 17/320016* (2013.01);
(Continued)

(58) Field of Classification Search
CPC ........... B26B 17/00; B26B 17/02; A01G 3/00; A01G 3/02; A01G 3/08; A01G 3/1047;
(Continued)

(56) References Cited

U.S. PATENT DOCUMENTS

| 437,647 A | * | 9/1890 | Franklin | B25B 9/02 |
| | | | | 294/99.2 |
| 720,706 A | * | 2/1903 | Lamb | B23D 27/02 |
| | | | | 30/241 |

(Continued)

FOREIGN PATENT DOCUMENTS

| DE | 962655 C | * | 4/1957 | | A01G 3/02 |
| DE | 19958264 A1 | * | 6/2001 | | B26B 17/00 |
| FR | 2823950 A1 | * | 10/2002 | | A01G 3/02 |

OTHER PUBLICATIONS

English Translation of DE19958264 A1 (Year: 2001).*
(Continued)

*Primary Examiner* — Jennifer B Swinney
(74) *Attorney, Agent, or Firm* — Douglas J. Ryder; Ryder, Mazzeo & Konieczny LLC

(57) ABSTRACT

A guillotine style cutting mechanism that can cut material without a pair of pivoting blades that are externally exposed, does not require a user to open and close two fingers to operate, and can be operated in both the left and right hands (not designed for either hand). The cutting mechanism includes a receiving inlet (trap) for receiving the material, a stationary blade within the trap and a moveable blade that enters the trap when activated by an engagement mechanism. The cutting mechanism may include an outer housing having an open interior, an extension arm extending from the housing to create the trap, a stationary blade within the trap, a movable blade formed on a rod within the housing, and an engagement button that causes the moveable blade to traverse the housing so as to extend into the trap and engage the stationary blade to cut the material.

18 Claims, 7 Drawing Sheets

(51) Int. Cl.
*A61B 17/04* (2006.01)
*A61B 17/3201* (2006.01)
*A61B 17/16* (2006.01)
*A61B 17/88* (2006.01)

(52) U.S. Cl.
CPC ....... *A61B 17/1611* (2013.01); *A61B 17/3201* (2013.01); *A61B 17/8863* (2013.01)

(58) Field of Classification Search
CPC  A01G 3/06; A01G 3/081; A24F 13/24; A24F 13/26
USPC .................................................. 30/241, 242
See application file for complete search history.

(56) References Cited

U.S. PATENT DOCUMENTS

| | | | | | |
|---|---|---|---|---|---|
| 1,540,392 | A * | 6/1925 | Grow | ............... | A01D 46/247 30/241 |
| 2,195,045 | A * | 3/1940 | Bernay | ............... | A01G 3/0255 144/34.5 |
| 2,270,495 | A * | 1/1942 | Bernay | ............... | A01G 3/0255 30/184 |
| 3,041,725 | A * | 7/1962 | Harries | ............... | A01G 3/033 30/180 |
| 3,844,291 | A * | 10/1974 | Moen | ............... | A61B 17/30 279/51 |
| 3,855,699 | A * | 12/1974 | Charlett | ............... | A01G 3/02 30/135 |
| 4,058,126 | A * | 11/1977 | Leveen | ............... | A61B 17/28 606/159 |
| 4,099,529 | A * | 7/1978 | Peyman | ............... | A61F 9/00763 30/241 |
| 4,106,508 | A * | 8/1978 | Berlin | ............... | A61B 17/1227 251/7 |
| 4,111,207 | A * | 9/1978 | Seiler, Jr. | ............... | A61F 9/00763 30/241 |
| 4,443,941 | A * | 4/1984 | McPhaul | ............... | A61B 17/8863 30/182 |
| 4,950,015 | A * | 8/1990 | Nejib | ............... | A61M 5/3213 128/919 |
| 5,176,695 | A * | 1/1993 | Dulebohn | ............... | A61B 17/320016 30/134 |
| 5,261,163 | A * | 11/1993 | Shearhart | ............... | A01G 5/00 30/135 |
| 5,407,243 | A * | 4/1995 | Riemann | ............... | A01M 3/00 294/100 |
| 6,374,498 | B1 * | 4/2002 | Liu | ............... | A01G 3/0255 30/211 |
| 2008/0154292 | A1 * | 6/2008 | Huculak | ............... | A61F 9/00763 606/167 |
| 2013/0211439 | A1 * | 8/2013 | Geuder | ............... | A61G 9/00763 606/171 |
| 2014/0005689 | A1 * | 1/2014 | Griffiths | ............... | A61B 17/0467 606/138 |
| 2015/0335485 | A1 * | 11/2015 | Rieger | ............... | A61F 9/00763 606/171 |
| 2016/0022489 | A1 * | 1/2016 | Hartstra | ............... | A61F 9/00763 606/166 |

OTHER PUBLICATIONS

Tauten Precision Line Cutter, Pro Elite, Tauten, Inc., date unknown, available prior to filing of provisional application at http://www.tautensports.com/the-tauten-precision-line-cutter-pro-elite/.

Silver Color Cigar Cutter Fathers Day Gift, Tungsten World, 2014, available at http://www.tungstenworld.com/Silver-Color-Cigar-Cutter-Fathers-Day-Gift/?gclid=Cj0KEQiA_eXEBRDP8fnlIJDXxsIBEiQ AAGfyoalQtepSzyAS2sihfMYau3UFZCfM9ypTAE65Abe8KX0aA hKa8P8HAQ&gclsrc=aw.ds.

* cited by examiner

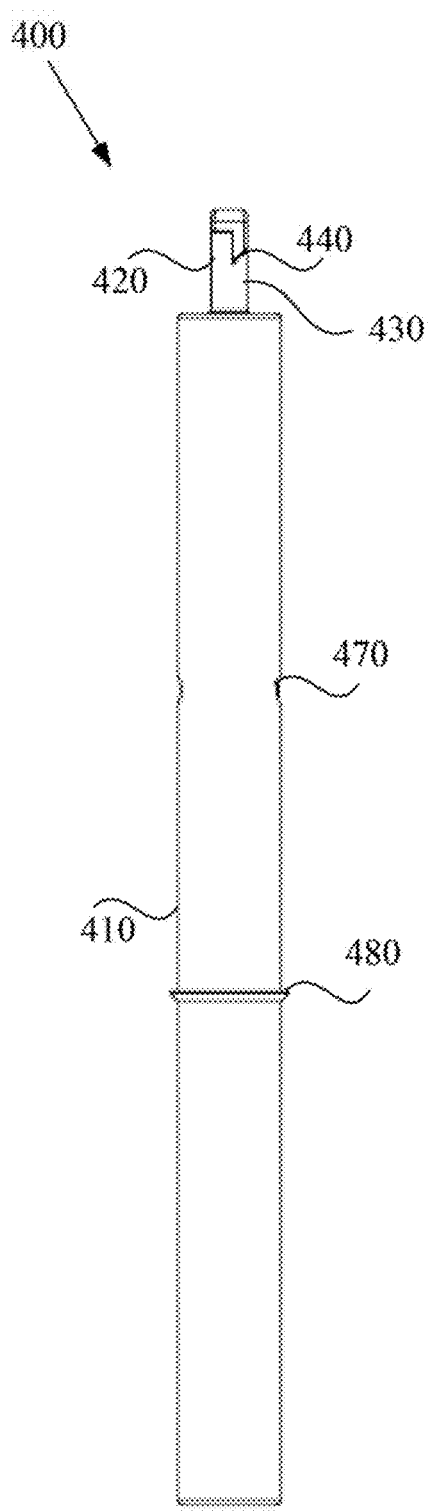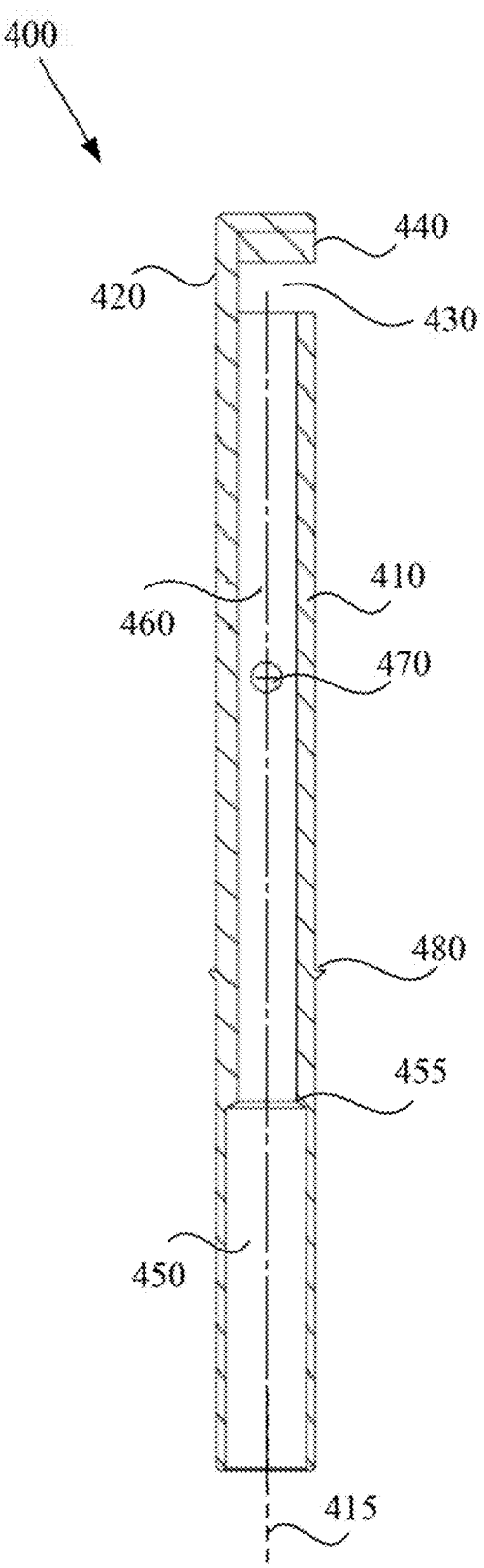
FIG. 4A
FIG. 4B

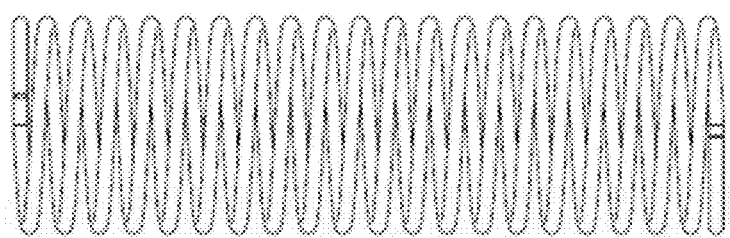
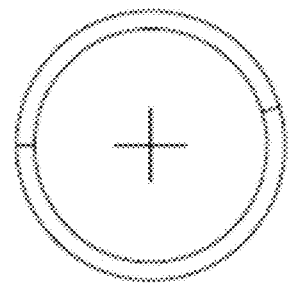
*FIG. 8A*  *FIG. 8B*
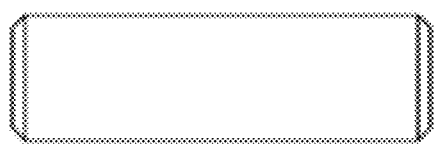
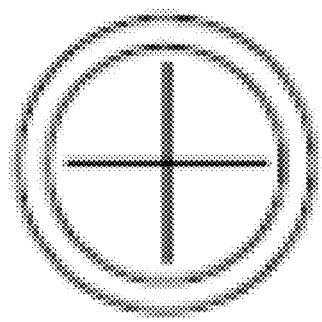
*FIG. 9A*  *FIG. 9B*

GUILLOTINE STYLE CUTTING MECHANISM

PRIORITY

This application claims the priority under 35 USC § 119 of Provisional Application 62/268,576 filed on Dec. 17, 2015, entitled "Guillotine Style Scissors" and having Todd Schwartz as inventor. Application 62/268,576 is herein incorporated by reference in its entirety.

BACKGROUND

Scissors are one of the most common cutting tools, used in various fields including arts and crafts, food preparation, personal hygiene, and medicine. Virtually all modern scissors, though having aesthetic and ergonomic differences, function essentially the same.

FIG. 1 illustrates a perceptive view of example scissors 100 that are typically used today. The scissors 100 include a first member 110 and a second member 120 that are overlaid on one another and pivotally connected around a generally central point 130. Each member 110, 120 includes one end that has sharpened edges (blades) 140, 150 and one end that has finger loops 160, 170 (the first member 110 includes blade 140 and finger loop 160 and the second member 120 includes blade 150 and finger loop 170). Separating the finger-loops 160, 170 causes the blades 140, 150 to separate and allows an object to be cut to enter therebetween. Bringing the finger-loops 160, 170 together causes the blades 140, 150 to come together, thereby producing a cutting or shearing force on the object in between the blades 140, 150.

The design of modern scissors allows them to be operated manually with one hand, though typically only the right due to the position of the blades (work poorly in the left hand since right side blade lies over the left). The operation of the scissors requires opening and closing of the hand (abduction and adduction). This hand movement is apt to be weak and prone to fatigue. Furthermore, it increases stress of the hand and wrist joints.

Depending on their intended use and field, the blades may be sharper to increase their cutting precision at the point of contact, or may be duller to increase safety in use. The ubiquity of scissors as a precision cutting tool has caused them to be adapted for specialized use in many different field, including the medical field. Scissors are particularly varied in the medical field because of the multitude of materials which they are used to cut, such as clothing, bandages, thread, skin, and sutures. To facilitate these functions, surgical scissors have some variability in design, including curved and/or longer blades to increase accessibility, blunted ends for safety, or sharper edges for extreme precision cutting. Despite these small design alterations, however, surgical scissors typically adhere to most common characteristics of typical scissors, and therefore also possess the same shortcomings. Regardless of length and sharpness, blades still pose a danger to a medical patient, particularly when a cut is being made close to vital organs or sensitive body parts. Risks persist of the scissors slipping or cutting too deep to result in further injury to the patient, despite utmost care taken by medical personnel. Attempting to minimize such risks by cutting with the blade tips only, however, also minimizes the scissors' effectiveness because the strongest cutting force is produced closest to the pivot point.

Modern scissors are also heavily reliant and stressful on the user's manual operation. As such, the type of blades, the strength of the user, the force exerted on the scissors, and the material being cut are all factors that may influence the scissors' effectiveness in a surgical setting, in addition to increasing the risk of injury to the user and the patient.

Scissors were designed to cut fabric and paper. The design of open-ended, converging blades work well for cutting and advancing the scissors on sheets of paper and fabric, however it is poorly designed for trapping and cutting stronger threads and sutures. The blades push stronger material forward, away from the blades, reducing cutting ability. The hinged converging blades are very susceptible to torque placed on the blades during use. This can separate the blades and reduce slicing force.

What is needed is a new form of surgical scissors that minimizes the risks of injury, unpredictability, and stress persistent with traditional forms of surgical scissors, while also improving their ability to function effectively as a surgical tool. Such a form of scissors is needed to be truly ambidextrous to be able to be used by virtually anyone without inhibitions to its functionality, to minimize the exposure of its blade to reduce the risk of injury to the user and patient, to operate easily to reduce stress on the user's hands, and to increase the strength and efficiency of the traditional cutting tool with respect to typical surgical needs.

BRIEF DESCRIPTION OF THE DRAWINGS

The features and advantages of the various embodiments will become apparent from the following detailed description in which:

FIGS. 4A-B illustrate different views of an example outer housing utilized in an example guillotine style cutting mechanism, according to one embodiment.

FIGS. 8A-B illustrate different views of an example spring utilized in an example guillotine style cutting mechanism, according to one embodiment.

FIGS. 9A-B illustrate different views of an example pin utilized in an example guillotine style cutting mechanism, according to one embodiment.

DETAILED DESCRIPTION

The current invention is a cutting mechanism that does not require a pair of pivoting blades as utilized in current scissors. The cutting mechanism does not require a user to open and close two fingers in order to operate. The cutting mechanism can be operated just as easily in the left and right hands (is not designed for either hand). The cutting mechanism does not utilize blades that are exposed external to the mechanism. The cutting mechanism provides a safe and efficient means for cutting material. The cutting mechanism utilizes a guillotine blade arrangement.

Figure 1:
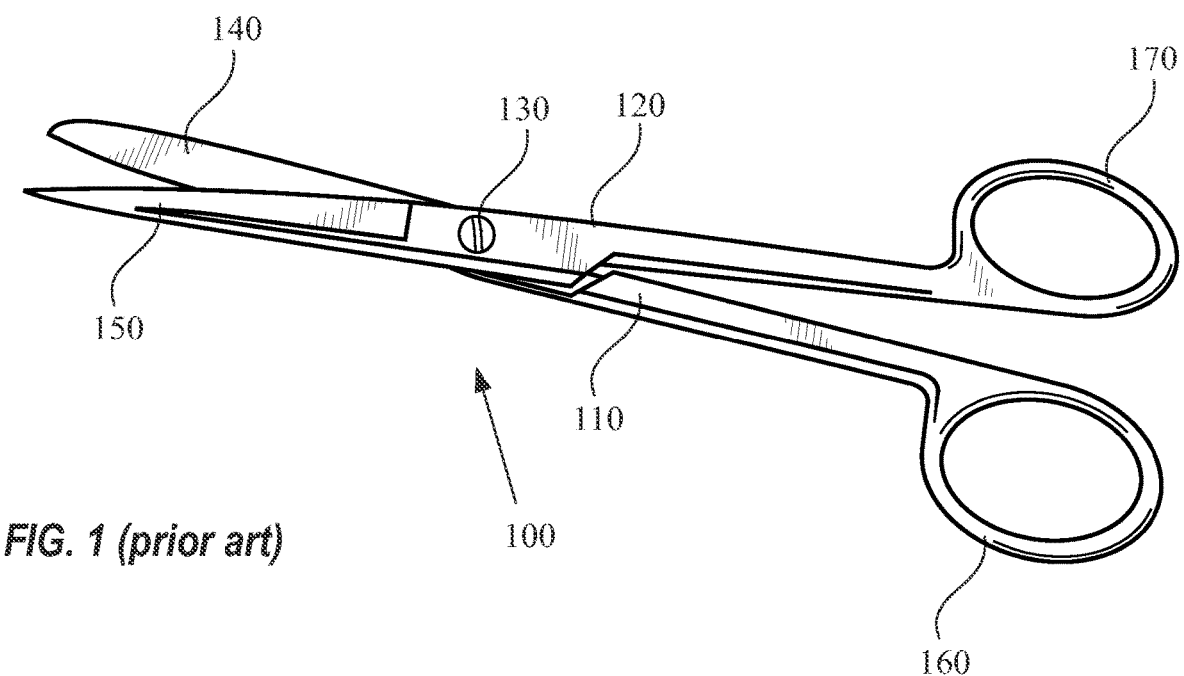
FIG. 1 illustrates a perceptive view of an example pair of scissors that are typically used today.
Figure 2:
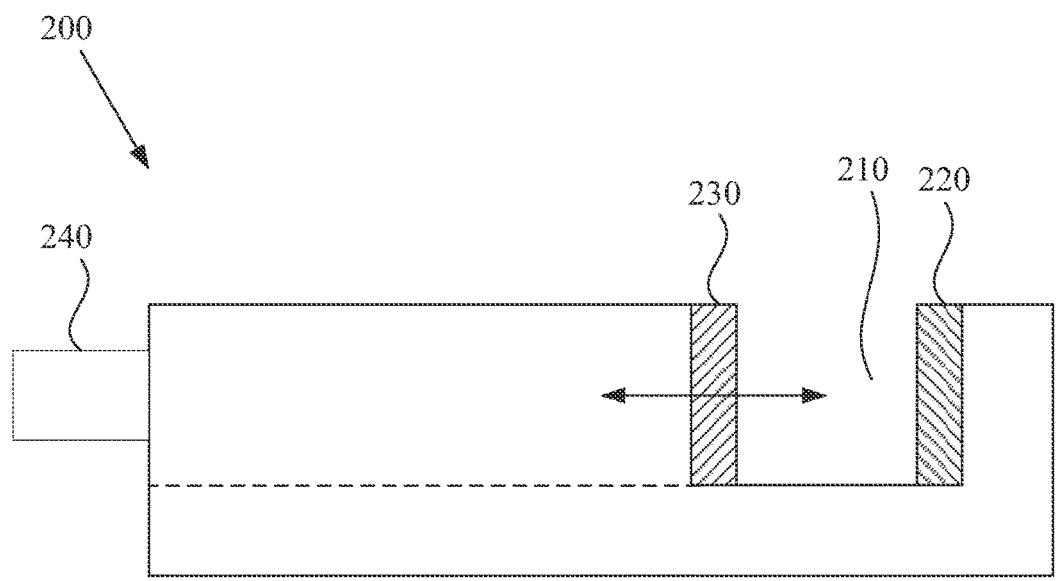
FIG. 2 illustrates a functional diagram of an example cutting mechanism for cutting material (e.g., thread, sutures), according to one embodiment.

FIG. 2 illustrates a functional diagram of an example cutting mechanism 200 for cutting material (e.g., thread, sutures), according to one embodiment. The cutting mechanism 200 includes a receiving inlet (trap) 210 formed therein for receiving the material and a guillotine blade arrangement for cutting the material. The guillotine blade arrangement includes a stationary blade 220 and a moveable blade 230 that come together to cut the material. The stationary blade 220 is located on one side of the trap 210 and the moveable blade 230 is located on (or in) an opposite side of the trap 210. An engagement mechanism 240 is utilized to activate the cutting mechanism 200 to move the moveable blade 230 into the trap 210 to engage with the stationary blade 220. When the moveable blade 230 engages the stationary blade 220 the material located therebetween is cut. As the blades are within the trap 210 the risk of inadvertent cutting or poking is greatly reduced (if not eliminated).

Figure 3A:
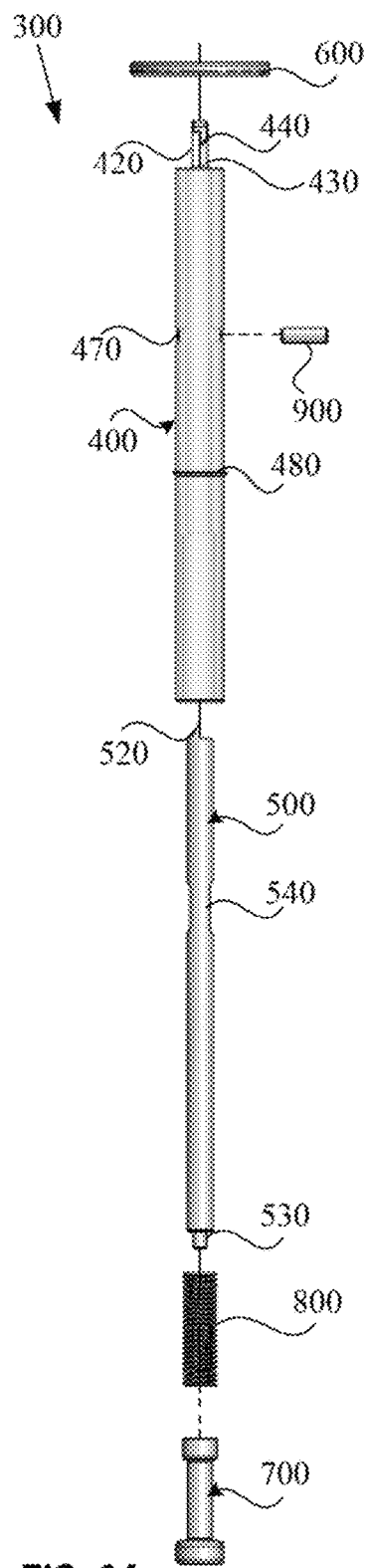
FIGS. 3A-C illustrate different views of an example guillotine style cutting mechanism, according to one embodiment.
Figure 3B:
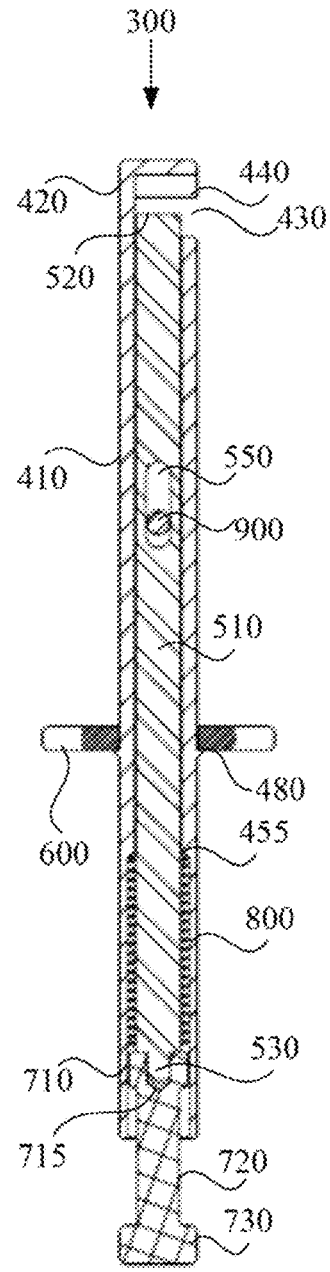
Figure 3C:
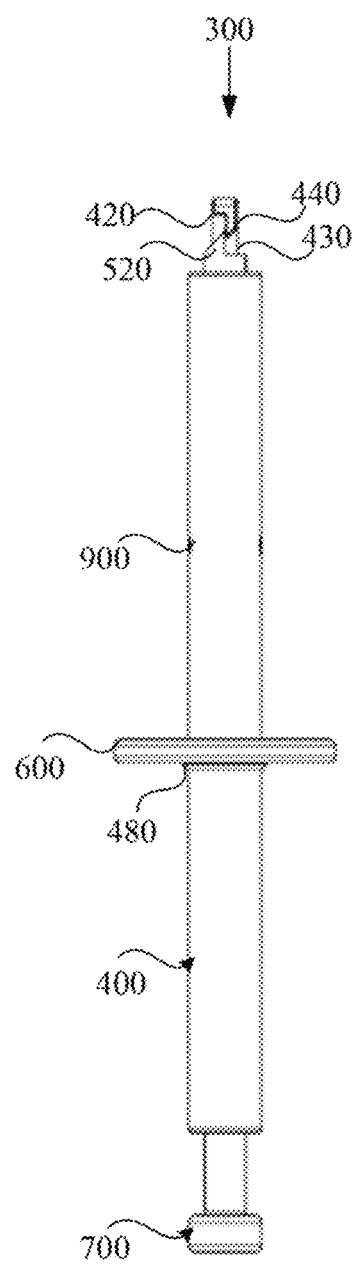
Figure 5A:
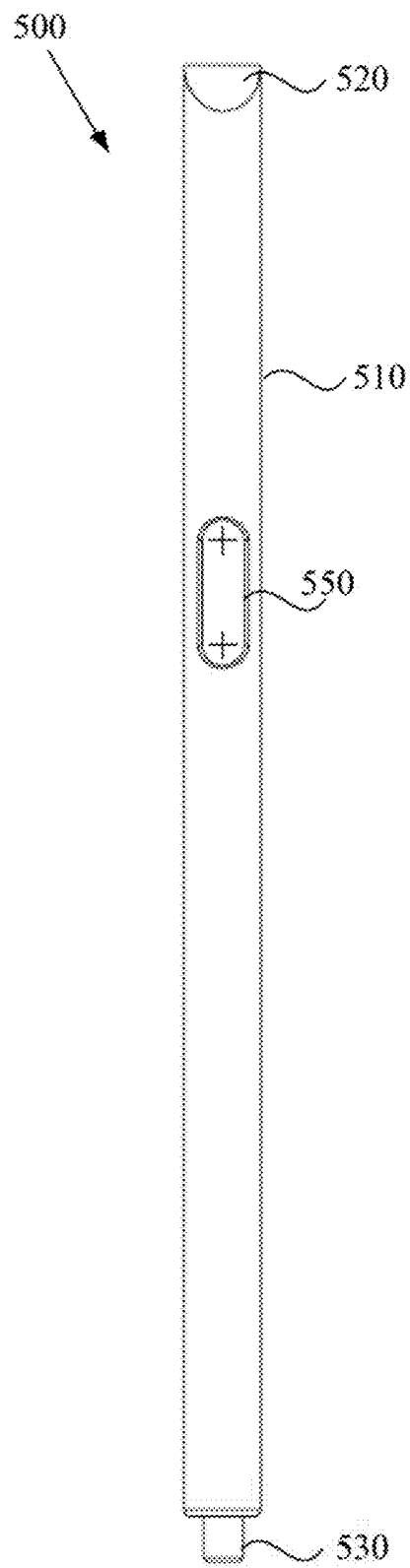
FIGS. 5A-D illustrate different views of an example internal movable rod utilized in an example guillotine style cutting mechanism, according to one embodiment.
Figure 5C:
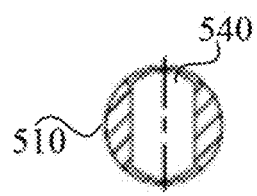
Figure 5D:
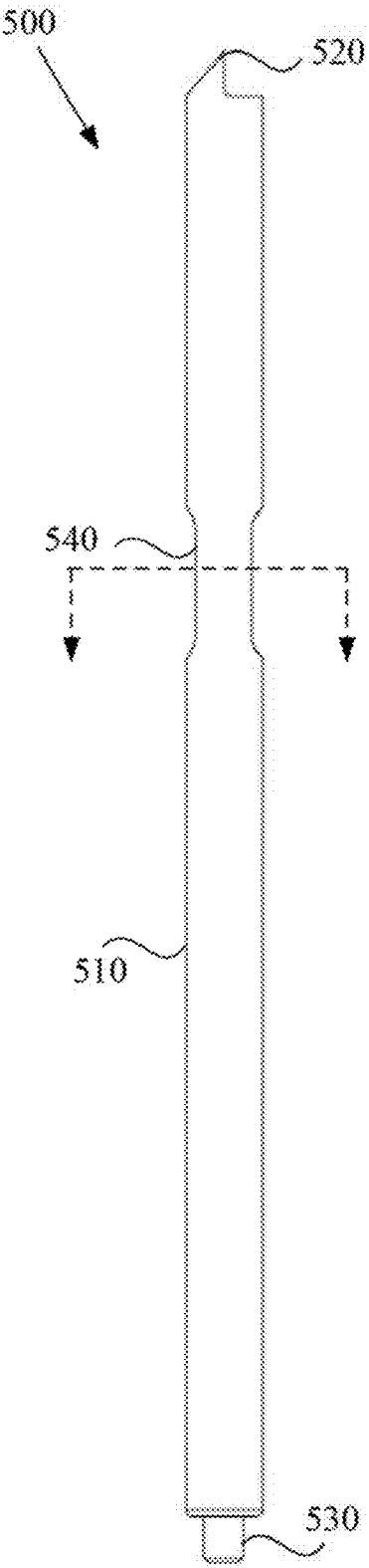
Figure 5B:
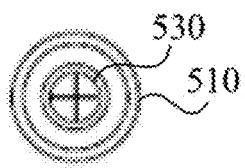

FIGS. 3A-C illustrate an exploded top view, a cross sectional right view and an exterior top view of an example guillotine style cutting mechanism 300, according to one embodiment. It should be noted that the views referred to herein are based on the where a trap (e.g., 210 of FIG. 2) will receive material (e.g., thread, sutures) to cut. For example, a top view means the trap would be accessible from the top and a right view means the trap would be accessible from the right. The cutting mechanism 300 includes an outer housing 400, an internal movable rod 500, a finger grip 600, an engagement button 700, a spring 800 and a set pin 900.

FIGS. 4A-B illustrate an exterior top view and a cross sectional right view of an example outer housing 400 utilized in an example cutting mechanism 300, according to one embodiment. The outer housing 400 includes a main body 410 having a generally circular cross section with a longitudinal axis 415 traversing in a first direction. An extension arm 420 extends past a first end of the main body 410. The extension arm 420 has a generally L-shaped cross section with a first portion traversing in the first direction (parallel to the longitudinal axis 415) and a second portion extending substantially parallel to the first portion. A receiving inlet (trap) 430 is created between the first end of the main body 410 and the extension arm 420. The trap 430 is to receive material to be cut. A stationary blade 440 is formed in (or located on) the second portion of the extension arm 420 facing the main body 410.

The main body 410 has an open interior including a first open portion 450 and a second open portion 460. The second open portion 460 is narrower than the first portion 450 so as to create a ledge 455 therewithin. Referring back to FIG. 3B, the open interior of the main body 410 houses the internal movable rod 500 and the spring 800 and partially houses the engagement button 700. The internal movable rod 500 is located in both the first open portion 450 and the second open portion 460 while the spring 800 is simply located in the second open portion 460. The spring 800 rests on the ledge 455 so that when pressure is applied from the second end (via the engagement button 700) it is compressed and when the pressure is removed it expands back to its steady state.

The main body 410 may also include a hole 470 formed therethrough for receiving the set pin 900. The main body 410 may also include a ridge 480 formed on an exterior thereof that may be used to support the finger grip 600.

FIGS. 5A-D illustrate an exterior right view, an exterior top view, a cross sectional view, and a bottom view of an example internal movable rod 500 utilized in an example cutting mechanism 300, according to one embodiment. The rod 500 has a body 510 that extends longitudinally in the first direction and includes a blade 520 at a first end thereof and a nub 530 at a second end. The body 510 includes a slot 550 formed therethrough. The slot 550 may be formed in a narrow section 540 of the body 510. The slot 550 is configured so that when it is in alignment with the hole 470 that the blade 520 is configured appropriately with respect to the stationary blade 440 (e.g., sharp edges of each blade 440, 520 aligned with respect to each other). When the rod 500 is within the housing 400, and the slot 550 and the hole 470 are aligned, the pin 900 can be received therein. The engagement of the pin 900 within the slot 550 and the hole 470 secures the rod 500 within the housing 400 but enables the rod 500 to be moved laterally (the distance of the slot 550) so the blade 520 can engage with the stationery blade 440 when activated. The engagement of the pin 900 within the slot 550 also keeps the rod 500 from rotating within the housing 400 (such rotation could leave the blade 520 and the stationary blade 440 not appropriately configured for efficiently cutting, or even cutting, a material within the trap 430).

The nub 530 has a smaller diameter than the body 510. The nub 530 may be received by the engagement button 700 and may be secured to the engagement button 700 in order to secure the engagement button 700 to the cutting mechanism 300 (partially within the housing 400). The nub 530 and the engagement button 700 may be secured via any number of known techniques. According to one embodiment, the nub 530 may be capable of snapping into the engagement button 700. According to one embodiment, the nub 530 may be threaded and be capable of being screwed into the engagement button 700. According to one embodiment, the nub 530 and the engagement button 700 may be secured to each other using, for example, an adhesive.

When the engagement button 700 is activated (pushed into the housing 400), the rod 500 is moved forward within the housing 400 so the blade 520 exits the main body 410, enters the trap 430 and engages the stationary blade 440. The engagement of the blade 520 and the stationary blade 440 results in the cutting of material located therebetween. FIGS. 3B and 3C illustrate the blade 520 exiting from the main body 410 and being within the trap 430.

Figure 6A:
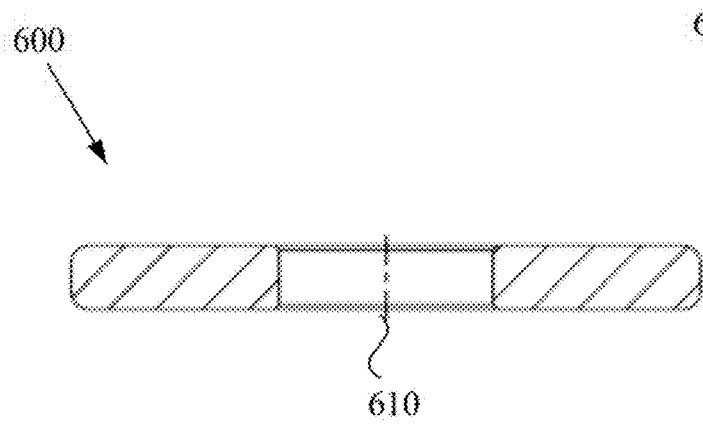
FIGS. 6A-B illustrate different views of an example finger grip utilized in an example guillotine style cutting mechanism, according to one embodiment.
Figure 6B:
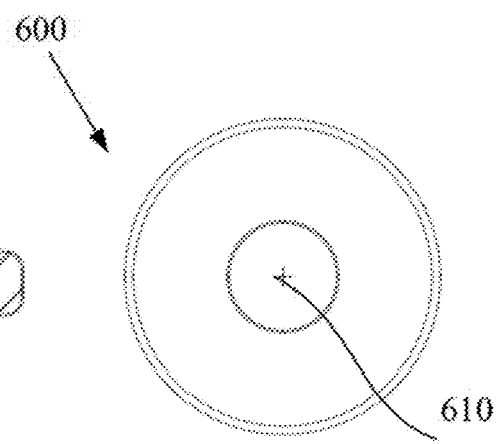

FIGS. 6A-B illustrate a cross sectional and a top view of an example finger grip 600 utilized in an example cutting mechanism 300, according to one embodiment. The finger grip 600 has a circular cross section and includes a hole 610 formed therein for receiving the main body 410. The finger grip 600 is in no way intended to be limited to be circular and could be other shapes or configurations without departing from the current scope. The finger grip 600 may have a size such that a finger of an average person may be received on each side of the main body 410.

The finger grip 600 may be installed over the main body 410 until it contacts the ridge 480. The finger grip 600 may be secured to the ridge 480 via any number of known techniques. According to one embodiment, the finger grip 600 may be secured to the ridge 480 using an adhesive or by fusing the two together (e.g., welding). The finger grip 600 may also be secured to the main body 410. According to one embodiment, there may not be a ridge 480 and the finger grip 600 may just be secured to the main body 410. According to one embodiment, the housing 400 may be formed having the finger grip 600 extend from the main body 410.

Figure 7A:
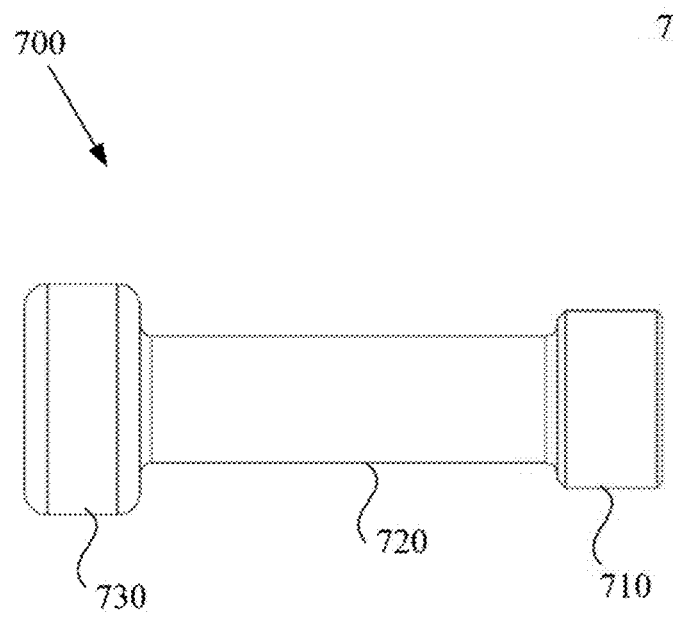
FIGS. 7A-B illustrate different views of an example engagement button utilized in an example guillotine style cutting mechanism, according to one embodiment.
Figure 7B:
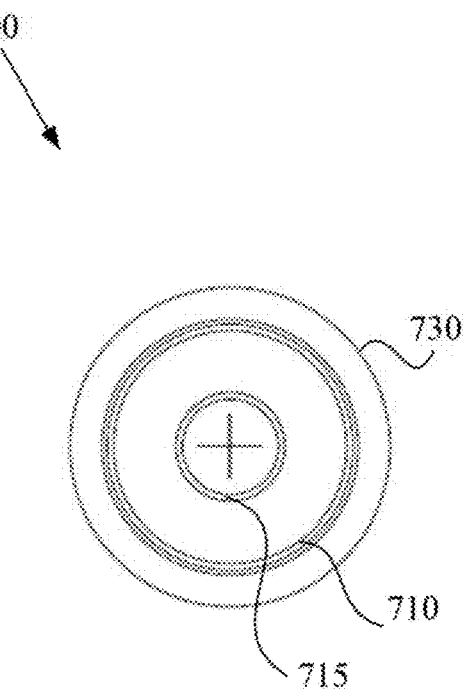

FIGS. 7A-B illustrate a side view and a top view of an example engagement button 700 utilized in an example cutting mechanism 300, according to one embodiment. The engagement button 700 may include a first end 710 for engaging the rod 500, a main body 720 and a second end 730 that is the portion a user interacts with. According to one embodiment, the second end 730 may be larger than the opening of the first open portion 450 so that it cannot be received within the housing 400. The first end 710 may have a hole 715 formed therein for receiving the nub 530 (FIG. 3B illustrates the nub 530 being received within the hole 715). The nub 530 and the hole 715 may be secured to each other via any number of known techniques. According to one embodiment, the nub 530 may be capable of snapping into the hole 715. According to one embodiment, the hole 715 may be threaded and be capable of having the nub 530 screwed thereinto. According to one embodiment, the nub 530 and the hole 715 may be secured to each other using, for example, an adhesive.

The first end 710 may abut the second end of the rod 500 and may also abut the spring 800 that is configured around the rod 500 (FIG. 3B illustrates the spring 800 around the rod 500). It should be noted that the engagement button 700 is not limited to having three sections with different circumferences as illustrated. For example, the main body 720 need not be thinner that the first end 710 (the main body 720 and the first end 710 could be same size). In fact, since the use of the pin 900 limits the lateral movement of the rod 500 within the housing 400, the second end 730 need not be bigger than opening of the first open portion 450. As such, the second end 730 could be the same size as the main body 720 and according to one embodiment the engagement button 700 may be the same size across its entirety (the first end 710, the main body 720 and the second end 730 may all be the same size).

FIGS. 8A-B illustrate side and top views of an example spring 800 utilized in an example cutting mechanism 300, according to one embodiment. The spring 800 is configured to be placed over the rod 500 and fit within the housing 400 (fit within the first open portion 450 and rest on the ledge 455). The spring 800 is configured to be contracted when the engagement button 700 is pushed in and to push the engagement button 700 out once the force on the engagement button 700 is removed.

FIGS. 9A-B illustrate side and top views of an example pin 900 utilized in an example cutting mechanism 300, according to one embodiment. The pin 900 is configured to fit within the hole 470 and the slot 550. After insertion, the pin 900 is to be secured to the housing 400 via any number of known techniques. According to one embodiment, the pin 900 may be secured to the housing 400 using an adhesive or by fusing the two together (e.g., welding).

Referring back to FIGS. 3A-C, one can see how the example cutting mechanism 300 is configured and operates. The spring 800 is inserted over the rod 500 and the engagement button 700 is connected to the rod 500. The engagement button 700 may be connected to the rod 500 by engaging the hole 715 and the nub 530. The rod 500, the spring 800 and the engagement button 700 are inserted into the housing 300. The spring 800 will rest on the ledge 455 within the housing 400. The rod 500 is rotated so that blade 520 is facing the right direction with respect to the stationary blade 440. The rod 500 is then adjusted to align the slot 550 with the hole 470. The pin 900 is inserted through the hole 470 and the slot 550 and is then secured to the housing 400.

The finger grip 600 is placed over the housing 400 until it contacts the ridge 480 and is then secured to the housing 400.

In order to operate the cutting mechanism 300, a user may place a finger on each side of the housing 400 and rest their fingers on the finger grip 600 (on side facing the blades 440,520). The user may then place their thumb against the engagement button 700 and use their thumb to push the engagement button 700 in order to activate the cutting mechanism 300. Alternatively, the user may place their palm against the engagement button 700 and use their fingers to pull the cutting mechanism 300 toward their palm and thus cause the engagement button 700 to be pushed in and the cutting mechanism 300 to be activated. Prior to activating the cutting mechanism 300, the user would position the cutting mechanism 300 such that the material to be cut was located within the trap 430.

The activation of the cutting mechanism 300 does not require the opening and closing of a user's hand (abduction and adduction) as is required with typical scissors. As previously noted, such an operation is apt to be weak, prone to fatigue and increases stress of the hand and wrist joints. The manner in which the cutting mechanism 300 is be operated, may enable a user to use them while they are performing other functions (possibly with the same hand). Additionally, the use of the stationary blade 440 and the moveable blade 520 as a guillotine arrangement within the trap 430 enables a user to cut the material without having blades exposed externally where they could potential cut or poke, for example, a patient.

According to one embodiment, the cutting mechanism 300 may be designed for continued use. In such an embodiment, the cutting mechanism 300 needs to be designed from materials that will be capable of continued use and maintain the necessary tolerances that would be required for effective operation. The blades 440, 520 would need to be designed such that they were capable of staying sharp for an extended period of time or that were capable of being resharpened or replaced. If the cutting mechanism 300 was to be used in a medical environment it would need to be designed such that it could be sterilized. According to one embodiment, the cutting mechanism 300 may be made of stainless steel.

According to one embodiment, the cutting mechanism 300 may be designed to be disposable. In such an embodiment, the cutting mechanism 300 would need to be made from materials that were relatively cheap but that were capable of having the cutting mechanism 300 remain operational to make a defined number of cuts. According to one embodiment, the cutting mechanism 300 may be made of plastic. If the cutting mechanism was to be used in a medical environment, the disposable cutting mechanism may come packaged in a sterile packaging material. Once the disposable cutting mechanism was used on that patient it would be disposed of.

It should be noted that the cutting mechanism 300 illustrated and described with respect to FIGS. 3-9 is not limited to the illustrated embodiments. For example, the manner in which the engagement button 700 and the rod 500 are connected to one another is not limited to the nub 530 and the hole 715, the manner in which the rod 500 is secured within the housing 400 is not limited to the pin 900 within the hole 470 and slot 550, and the location of the trap 430 is not limited to being at the end of the housing 400. According to one embodiment, the rod 500 could include a hole and the engagement button could include a nub to secure the engagement button 700 and the rod 500. According to one embodiment, the trap 430 could be formed as an opening within the main body 410.

Furthermore, a guillotine style cutting mechanism is not limited to a push button configuration having an engagement button located on the bottom of the device as illustrated and described with respect to FIGS. 2-9. According to one embodiment, the device may be activated via an engagement button located on the side of the device. Such a configuration, would need to transfer the direction of the push interaction from the side of the device to the front of the device by one of various means that are known.

Moreover, a guillotine style cutting mechanism is not limited to location and configuration of moveable and stationary blades (moveable blade being closer to the engagement mechanism and being pushed into the trap) as illustrated and described with respect to FIGS. 2-9. According to one embodiment, the stationary blade could be located on a side of the trap closer to the engagement mechanism and the moveable blade could be located on a side of the trap farther away and be pulled into the trap when the engagement mechanism is activated. According to one embodiment, the stationary blade could be located on a bottom of the trap and the moveable blade could pivot downward to engage along the bottom of the trap. According to one embodiment, both blades may be moveable blades that engage somewhere in the middle of the trap.

Additionally, a guillotine style cutting mechanism is not limited to use of an engagement button as illustrated and described with respect to FIGS. 2-9. According to one embodiment, the cutting mechanism may be activated using a pair of gripping handles.

Figure 10:
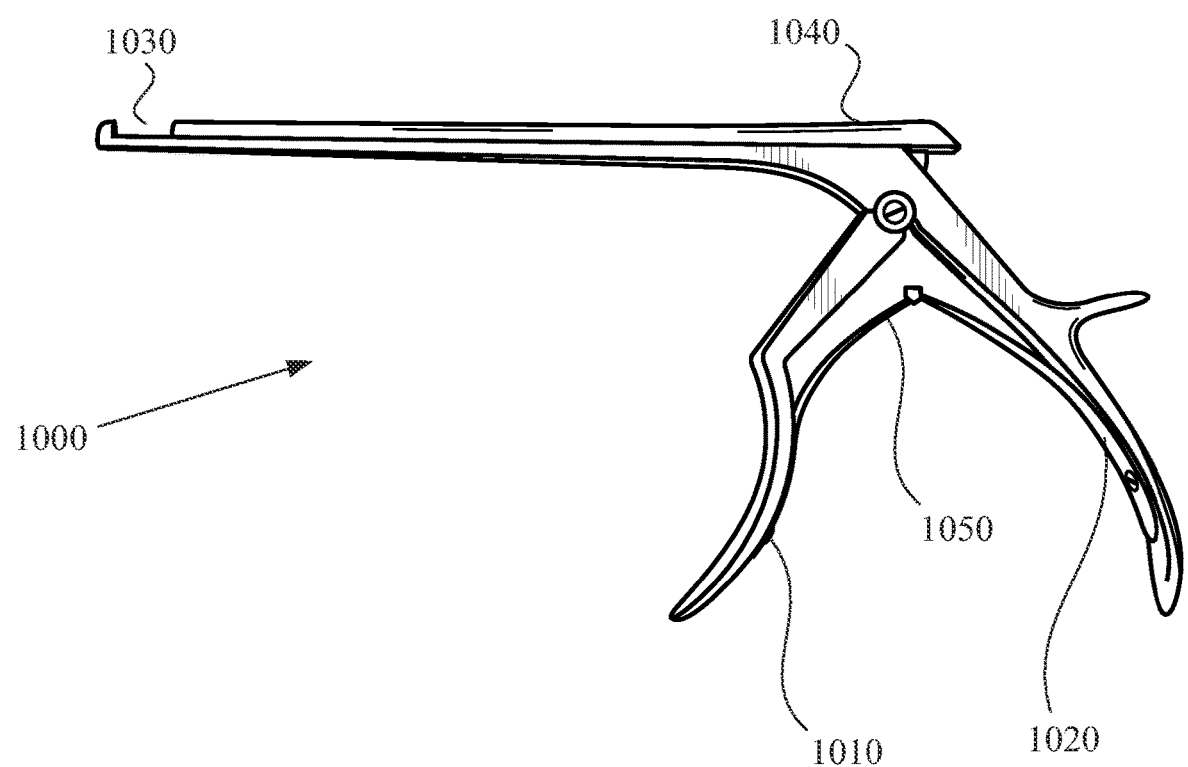
FIG. 10 illustrates a side view of an example guillotine style cutting mechanism utilizing gripping handles, according to one embodiment.

FIG. 10 illustrates a side view of an example guillotine style cutting mechanism 1000 utilizing gripping handles, according to one embodiment. The cutting mechanism 1000 includes a pair gripping handles 1010, 1020 that when engaged (pulled together) cause a moveable blade (not specifically identified) to enter a trap 1030 and engage with the stationary blade (not specifically identified) that may be located therewithin. When a first handle 1010 is pulled toward a second handle 1020 it may cause an upper portion 1040 that may include the moveable blade to pivot forward into the trap 1030 in order to cut material located therewithin. A spring mechanism 1050 may be located between the handles 1010, 1020 in order to push the first handle 1010 away from the second handle 1020 when pressure is removed therefrom in order to return the first handle 1010 to its steady state and to retract the upper portion 1040 from the trap 1030.

The description above and the accompanying drawings may reference and depict specific and relative dimensions and configurations of the invention, as well as referencing specific constituent materials and uses for the invention. The invention, however, is not limited to those dimensions, materials, or uses. The dimension and configuration choices made in the description and the accompanying drawings were merely descriptive and do not serve to limit the invention to those dimensions. Although the invention has been illustrated by reference to specific embodiments, it will be apparent that the disclosure is not limited thereto as various changes and modifications may be made thereto without departing from the scope. Reference to "one embodiment" or "an embodiment" means that a particular feature, structure or characteristic described therein is included in at least one embodiment. Thus, the appearances of the phrase "in one embodiment" or "in an embodiment" appearing in various places throughout the specification are not necessarily all referring to the same embodiment.

The various embodiments are intended to be protected broadly within the spirit and scope of the appended claims.

The invention claimed is:

1. A handheld guillotine cutting apparatus configured to be held in, and operated by, only one hand of a user, the apparatus comprising
an external housing traversing along a longitudinal axis, the external housing having an open interior traversing from a first end to a second end along the longitudinal axis;
a finger grip secured to an exterior of the external housing, wherein the finger grip is configured to provide the user a location to place one or more fingers from the only one hand when the external housing is held in the only one hand of the user;
a receiving inlet formed in the first end of the external housing to receive an item to be cut;
a first blade located within the receiving inlet, wherein the first blade remains stationary;
a second blade located on a first end of a moveable rod located within the open interior of the external housing, wherein the moveable rod is in axial alignment with the external housing and is configured to move within the open interior along the longitudinal axis, and wherein the second blade is configured to enter the receiving inlet and engage the first blade with sufficient force in order to cut the item located in the receiving inlet; and
a push button having a first end located within the open interior in communication with a second end of the moveable rod and a second end extending from the second end of the external housing, wherein the push button is in axial alignment with the external housing, wherein the push button is configured such that a thumb or a palm of the only one hand of the user can be utilized to engage with the second end of the push button when the external housing is held in the only one hand of the user with the one or more fingers on the finger grip, wherein the push button is configured to advance the first end within the open interior along the longitudinal axis toward the first end of the external housing when the second end is pushed by the thumb or the palm of the only one hand of the user toward the external housing, wherein the moveable rod is configured to advance toward the first end of the external housing so that the second blade enters the receiving inlet with sufficient force to engage the first blade and cut the item located in the receiving inlet when the first end of the push button advances into the open interior.

2. The apparatus of claim 1, further comprising a spring configured to compress when the thumb or the palm of the only one hand of the user pushes the second end of the push button towards the external housing and to decompress when the thumb or the palm of the only one hand of the user releases the push button, wherein the decompressing of the spring causes the first end of the push button and the moveable rod to move toward the second end of the external housing and the second blade to be retracted from the receiving inlet.

3. The apparatus of claim 1, wherein the first blade is located on a first side of the receiving inlet and the second blade enters via a second side opposite the first side.

4. A handheld guillotine cutting apparatus configured to be held in, and operated by, only one hand of a user, the apparatus comprising an external housing traversing along a longitudinal axis, the external housing having an open interior traversing from a first end to a second end along the longitudinal axis;

an extension arm extending from the first end of the external housing, wherein a receiving inlet is formed between the first end of the external housing and the extension arm, wherein the receiving inlet is to receive an item to be cut;

a stationary blade located within the receiving inlet;

a finger grip secured to an exterior of the external housing, wherein the finger grip is configured to provide the user a location to place one or more fingers from the only one hand when the external housing is held in the only one hand of the user;

a movable rod located within the open interior of the external housing, wherein the moveable rod is in axial alignment with the external housing and is configured to traverse the open interior of the external housing along the longitudinal axis;

a movable blade located on a first end of the moveable rod, wherein the moveable blade is configured to exit the first end of the external housing and enter the receiving inlet and engage the stationary blade in order to cut the item located in the receiving inlet; and a push button having a first end and a second end, wherein the first end of the push button is located within the open interior of the external housing and is in communication with a second end of the moveable rod, wherein the second end of the push button is extending from the second end of the external housing, wherein the push button is configured such that a thumb or a palm of the only one hand of the user can be utilized to engage with the second end thereof when the external housing is held in the only one hand of the user and the one or more fingers are placed on the finger grip, wherein the push button is configured to advance the first end within the open interior along the longitudinal axis toward the first end of the external housing when the second end is pushed by the thumb or the palm towards the external housing, wherein the moveable rod is configured to advance within the open interior of the external housing toward the first end so that the movable blade enters the receiving inlet with sufficient force to engage the stationary blade and cut the item located in the receiving inlet when the first end of the push button advances into the open interior.

5. The apparatus of claim 4, further comprising a spring configured to compress when the thumb or the palm of the only one hand of the user pushes the second end of the push button towards the external housing and to decompress when the thumb or the palm of the only one hand of the user releases the push button, wherein the decompressing of the spring causes the first end of the push button and the moveable rod to move toward the second end of the external housing and the moveable blade to be retracted from the receiving inlet.

6. The apparatus of claim 4, wherein the stationary blade is located on a first side of the receiving inlet that faces the first end of the external housing and the movable blade enters via a second side that is aligned with the first end of the external housing.

7. The apparatus of claim 4, wherein
the external housing includes a hole formed therethrough perpendicular to the longitudinal axis; and
the moveable rod includes a longitudinal slot formed through a portion thereof; and further comprising a set pin that traverses the hole and the longitudinal slot, wherein the set pin enables the moveable rod to longitudinally traverse the open interior of the external housing without rotating therewithin to ensure appropriate alignment of the stationary blade and the movable blade is maintained.

8. The apparatus of claim 4, wherein the open interior of the external housing includes a first open portion and a second open portion that is narrower than the first open portion, and further comprising a spring located in the first portion that is configured to be compressed when the thumb or the palm of the only one hand of the user pushes the second end of the push button towards the external housing and to decompress when the thumb or the palm of the only one hand of the user releases the push button, wherein the decompressing of the spring causes the first end of the push button and the moveable rod to move toward the second end of the external housing and the moveable blade to be retracted from the receiving inlet.

9. A handheld guillotine cutting apparatus configured to be held in, and operated by, only one hand of a user, the apparatus comprising
an external housing traversing along a longitudinal axis, the external housing having an open interior traversing from a first end to a second end along the longitudinal axis, wherein the open interior includes a first open portion extending from the first end and a second open portion extending from the second end, wherein the first open portion is narrower than the second open portion, and wherein a ledge is formed within the open interior at a transition between the first open portion and the second open portion;

a receiving inlet extending from the first end of the external housing, wherein the receiving inlet is to receive an item to be cut;

a stationary blade located within the receiving inlet;

a finger grip secured to an exterior of the external housing, wherein the finger grip is configured to provide the user a location to place one or more fingers when the external housing is held in the only one hand of the user between the one or more fingers;

a movable rod located within the first open portion and the second open portion of the external housing, wherein the moveable rod is in axial alignment with the external housing, wherein the moveable rod is configured to traverse the open interior of the external housing along the longitudinal axis;

a movable blade located on a first end of the moveable rod;

a push button having a first end located within the second open portion of the external housing in communication with a second end of the moveable rod and a second end extending from the second end of the external housing, wherein the push button is configured such that a thumb or a palm of the only one hand of the user can be utilized to engage with the second end thereof when the external housing is held in the only one hand of the user between the one or more fingers and the one or more fingers are placed on the finger grip, wherein the push button is configured to advance the first end within the open interior along the longitudinal axis toward the first end of the external housing when the second end is pushed towards the external housing by the thumb or the palm of the only one hand, wherein the moveable rod is configured to advance toward the first end of the external housing so that the movable blade enters the receiving inlet and engages the stationary blade with sufficient force to cut the item located in the receiving inlet when the first end of the push button advances within the open interior; and a spring located within the second open portion of the external housing, wherein a first end of the spring is in communication with the ledge and a second end of the spring is in communication with the push button, wherein the spring is configured to compress when the thumb or the palm of the only one hand of the user pushes the second end of the push button towards the external housing and to decompress when the thumb or the palm of the only one hand of the user releases the second end of the push button, wherein the decompressing of the spring causes the second end of the push button to be pushed outward, the moveable rod to be moved toward the second end of the external housing and the moveable blade to be retracted from the receiving inlet.

10. The apparatus of claim 9, wherein the external housing includes a hole formed therethrough perpendicular to the longitudinal axis; and the moveable rod includes a longitudinal slot formed through a portion thereof; and further comprising a set pin secured within the hole and the longitudinal slot, wherein the set pin is utilized to secure the external housing and the moveable rod together in an appropriate configuration to ensure appropriate alignment of the stationary blade and the movable blade is maintained and to enable the moveable rod to longitudinally traverse the open interior of the external housing.

11. The apparatus of claim 9, wherein the external housing includes a ledge on an outer portion to secure the finger grip.

12. The apparatus of claim 9, wherein the second end of the moveable rod includes a nub and the first end of the push button includes a hole for receiving the nub, wherein the nub and the hole are to secure the moveable rod and the push button together.

13. The apparatus of claim 9, wherein the stationary blade is located on a first side of the receiving inlet that faces the first end of the external housing and the movable blade enters the receiving inlet via a second side that is aligned with the first end of the external housing.

14. The apparatus of claim 9, wherein the items to be cut include sutures and stitches for a patient.

15. The apparatus of claim 9, wherein the receiving inlet is formed within an extension arm that extends outward from the first end of the external housing.

16. The apparatus of claim 9, further comprising a first arm that extends outward from a first side of the first end of the external housing substantially parallel to the longitudinal axis and a second arm that extends substantially perpendicular from an end of the first arm in a direction toward a second side of the first end of the external housing, wherein the receiving inlet is formed between the first end of the external housing, the first arm and the second arm, and wherein the stationary blade is located on the second arm facing the first end of the external housing.

17. The apparatus of claim 9, wherein the moveable rod is configured to not rotate within the open interior of the external housing so the moveable blade and the stationary blade remain aligned.

18. The apparatus of claim 9, wherein the apparatus is configured to be held in, and operated by a left hand or a right hand of the user.

* * * * *